US00PP12489P2

(12) United States Plant Patent
Utecht

(10) Patent No.: US PP12,489 P2
(45) Date of Patent: Mar. 26, 2002

(54) GERANIUM PLANT NAMED 'FISFIRE'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/772,845

(22) Filed: Jan. 31, 2001

(51) Int. Cl.[7] ..... A01H 5/00
(52) U.S. Cl. ..... Plt./330
(58) Field of Search ..... Plt./330, 328

(56) References Cited

PUBLICATIONS

German Application for 'Fisfire' Sep. 15, 1998.
German Denomination for 'Fisfire' Sep. 15, 1999.
*Plant Varieties Journal*, No. 38, Jan. 2001, pp. 50–51 (Canada).
European Community Application—'Fisfire' (Oct. 15, 1999).
European Community Denomination—'Fisfire' (Oct. 15, 1999).
European Community Grant—'Fisfire' (#6817) (Feb. 15, 2001).
GTITM UPOVROM Citation for 'Fisfire' as per QZ PBR 991048; Jul. 20, 1999.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisfire', as described and illustrated, and particularly characterized by the combined features of round, semi-double, brilliant scarlet flowers, large, semi-spherically shaped umbels, medium-green foliage with distinct zonation, medium-sized or taller, round, and well-branched plant habit, and medium spring flowering response.

1 Drawing Sheet

BACKGROUND OF THE INVENTION

The present invention comprises a new and distinct cultivar of geranium, botanically known as *Pelargonium zonale*, and hereinafter referred to by the cultivar name 'Fisfire'.

'Fisfire' is a product of a planned breeding program which had the objective of creating new geranium varieties with scarlet flower color, medium-green foliage, and moderately vigorous growth. 'Fisfire' originated from a hybridization made by the inventor Angelika Utecht in a controlled breeding program in Galdar, Gran Canaria, Spain, in 1995.

The female parent was a hybrid seedling, No. 990-1 (unpatented), derived from a cross between 'Fisnida' (unpatented and 'Volcano' (U.S. Plant Pat. No. 5,940). Both varieties have orange-red flowers, the former single-type flowers, the latter semi-double flowers. The male parent of 'Fisfire' was the variety 'Fistador', United States plant patent applied for, Ser. No. 09/323,149, characterized by scarlet semi-double flowers, zoned foliage, and medium-tall, round plant habit.

'Fisfire' was selected as one flowering plant within the progeny of the stated cross by Angelika Utecht in 1996 in a controlled environment in Galdar, Gran Canaria, Spain. The first act of asexual reproduction of 'Fisfire' was accomplished when vegetative cuttings were taken from the initial selection in the fall of 1996 in a controlled environment in Galdar, Gran Canaria, Spain, by, or under the supervision of, Angelika Utecht.

Horticultural examination of plants grown from cuttings of the plant initiated in May 1997 in Hillscheid, Federal Republic of Germany, and continuing thereafter, has demonstrated that the combination of characteristics as herein disclosed for 'Fisfire' are firmly fixed and are retained through successive generations of asexual reproduction.

'Fisfire' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditons which approximate those generally used in commercial practice.

The following traits have been repeatedly observed and are determined to be basic characteristics of 'Fisfire' in combination distinguish this geranium as a new and distinct cultivar:

1. Very brilliant scarlet colored, rounded, semi-double flowers;

2. Large, semi-spherically shaped umbels;

3. Medium green foliage with very strong zonation;

4. Round and very well-branched habit, somewhat over medium sized; and

5. Medium, mid-season spring flowering response.

Of the many commercial cultivars known to the present inventor, the most similar in comparison to 'Fisfire' is the parental variety 'Fistador'.

In comparison to 'Fistador', 'Fisfire' has an even more brilliant flower color, similarly shaped flowers, wider umbels, larger leaves with stronger zonation on leaves, and somewhat taller plant habit.

The female parent of 'Fisfire' had single-type flowers, large umbels, brilliant red flower color, medium sized plant habit and middle green foliage with relatively strong zonation. In comparison to 990-1, 'Fisfire' has semi-double flowers and a somewhat deeper shade of red flower color.

BRIEF DESCRIPTION OF THE DRAWING

The accompanying photographic drawing shows typical flower and foliage characteristics of 'Fisfire' with colors being as true as possible with an illustration of this type. The measurements were taken in Langley, British Columbia, Canada, on Jul. 20, 2000, 15 weeks after planting of rooted cuttings into 6 inch pots. The plants had not been pinched.

In the following description color references are made to The Royal Horticultural Society Colour Chart (R.H.S.). The color values were determined indoors from plants developed in a green-house in May, 2000, in Hillscheid, Germany.

Classification:

*Botanical.*—A hybrid of the species *Pelargonium zonale* L'Hérit.

*Commerical.*—Zonal geranium, cv. 'Fisfire'.

Inflorescence:

*Umbel.*—Shape: Semi-spherical. Average diameter: 121 mm. Average depth: 60–65 mm. Peduncle length: 158 mm. Peduncle color: Grass-green, from RHS 143 B to RHS 143 C. Pedicel length: 37.5 mm. Pedicel color: Mainly green, RHS 143 A, upper end reddish RHS 179 A. Number of flowers per umbel: Approximately 25–30. Lastingness of the umbel: Approximately 18 days at 18° C.

*Corolla.*—Average diameter: 44 mm. Form: Semi-double. Shape: Round, slightly cup-sphaped. Number of petals: 9–10. Petal size: Upper petals 22–23 mm long, 18–22 mm wide, lower petals 22–23 mm long and 20–22 wide. Petal shape: Obovate, attenuate base, upper end rounded, margin entire. Number of petaloids: 0–1. Color of petaloids: Upper surface RHS 43 A, lower surface RHS 43 B. Color (general tonality from a distance of three meters): Scarlet. Color of upper petals: from RHS 43 A to RHS 44 A. Markings of upper petals: Absent. Color of lower petals: from RHS 43 A to RHS 44 A, no markings. Color of lower surface of petals: Mainly RHS 43 A. Color of sepals: Green, RHS 143 A, reddish base RHS 181 A. Number of sepals: 5.

*Bud: (just before petals unfold ).*—Shape: Broad elliptical. Sepal Color (lower part); Mainly green, from RHS 143 A to RHS 143 B, slightly reddish at the base RHS 179 A on outer surface, light green RHS 143 C with RHS 179 B at the base on inner surface. Size of sepals: 10–12 mm in length, 4 mm in diameter for the largest upper sepal, 2–3 mm in diameter for the other sepals. Shape of sepals: Linear to laneolate, acute tip, base truncate, surface weak with pubescence, margin entire. Petal Color (upper part): Orange-red RHS 43 A. Length: 15–16 mm. Width: 10–11 mm.

*Reproductive organs.*—Androecium: 5–7 fertile anthers, white filaments, yellow-orange pollen RHS 30 A, plentiful quantity of pollen produced. Gynoecium: 5–6-lobed red stigma, red style, one pistil per flower. Fertility/seed set: A few seeds are developed, mainly from late summer on, oblong in shape, 4–5 mm long, brown RHS 177 B in color.

*Spring flower response period.*—In Hillscheid, Germany, in 2000, average 0.9 flowers opened 8 weeks after planting of rooted cuttings.

*Outdoor flower production.*—Medium to rich flowering, the flower count in 2000, in Hillscheid, Germany, indicated about 4 inflorescences per plant in mid May.

*Durability.*—Good stability of flower color (no fading), no shattering, somewhat susceptible to being scorched by intense sunlight, which is typical of varieties with intense red flower color, relatively good rain resistance.

*Lastingness of the individual bloom.*—Approximately 9 days at 18° C.

*Fragrance.*—None.

Plant:

*Foliage.*—Form: Kidney-shaped, with nearly closed base. Margin: Bicrenated, wavy. Apex: Almost round, very weak lobes. Base: Cordate with nearly closed gap. Texture: Slightly velvety on upper surface. Size of leaf: 100 mm wide, 65 mm long. Color of upper surface: Medium-green, approximatley from RHS 137 B to RHS 137 C. Color of zonation: Very strong, brown, about RHS 166 A. Petiole size: 55–65 mm in length, 3 mm in diameter. Petiole color: RHS 143 C.

*General appearance and form.*—Stem color: Green, RHS 143 A. Internode length: 10–15 mm. Branching pattern: 7.5 branches. Plant size: 23.5 cm in height as measured from the soil to the surface of the foliage, 37.5 cm wide.

Disease pest resistance susceptibility: None observed to date.

I claim:

1. A new and distinct cultivar of geranium plant named 'Fisfire', as described and illustrated.

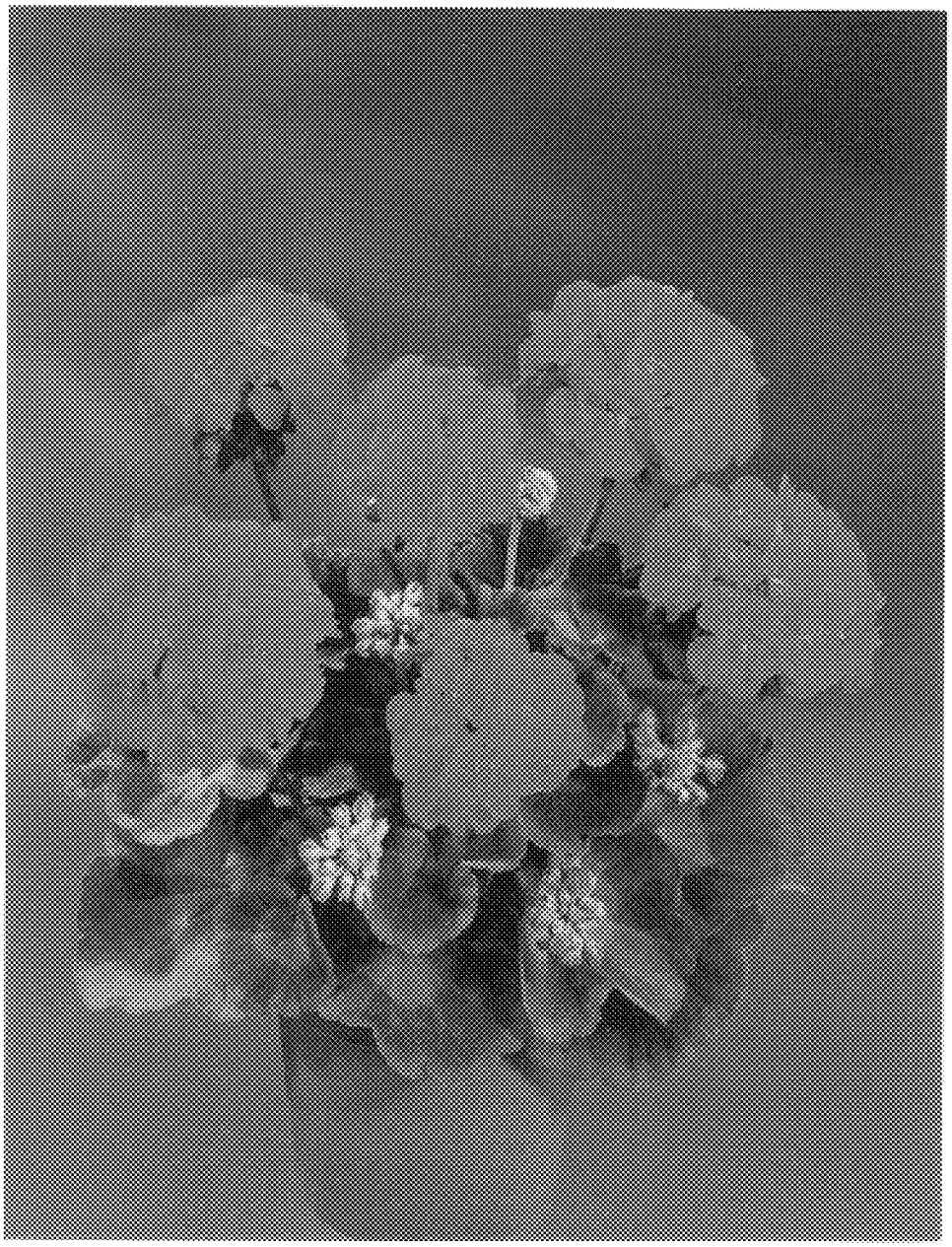

* * * * *